United States Patent [19]

Bertleff et al.

[11] Patent Number: 5,012,006
[45] Date of Patent: Apr. 30, 1991

[54] PREPARATION OF 2,2-DIALKYLPROPIONALDEHYDES

[75] Inventors: Werner Bertleff, Viernheim; Dieter Koeffer, Weinheim, both of Fed. Rep. of Germany

[73] Assignee: BASF Aktiengesellschaft, Ludwigshafen, Fed. Rep. of Germany

[21] Appl. No.: 466,931

[22] Filed: Jan. 18, 1990

[30] Foreign Application Priority Data

Feb. 1, 1989 [DE] Fed. Rep. of Germany ....... 3902892

[51] Int. Cl.$^5$ .................... C07C 45/49; C07C 45/50
[52] U.S. Cl. .................................. 568/451; 568/451
[58] Field of Search .......................... 568/451, 454

[56] References Cited

U.S. PATENT DOCUMENTS

| 4,593,126 | 1/1986 | Cornils et al. | 568/454 |
| 4,599,323 | 7/1986 | Demay et al. | 568/454 |

FOREIGN PATENT DOCUMENTS

| 0096986 | 12/1983 | European Pat. Off. | 568/454 |
| 0350921 | 1/1990 | European Pat. Off. | 568/454 |
| 1247125 | 9/1971 | United Kingdom | 568/451 |

OTHER PUBLICATIONS

Chemical Engineering Progress, vol. 62, No. 4, pp. 74–78, Apr. 1966, J. E. Knap et al., "Hydroformylation of Isobutene".

Zhurnal Prikladnoi Khimii, vol. 41, No. 10, 1968, pp. 2275–2281, Oct., 1968, (corr. J. of Applied Chem. of the USSR, pp. 2148–2152, V. Yu. Ganken et al., "Hydroformylation of Olefins in the Presence of Rhodium Carbonyls".

Chemical Abstracts, vol. 70, 1969 114537f, K. A. Alekseeva et al., "Composition of Isobutylene Hydroformylation Products".

Primary Examiner—Werren B. Lone
Attorney, Agent, or Firm—Oblon, Spivak, McClelland, Maier & Neustadt

[57] ABSTRACT

2,2-Dialkylpropionaldehydes I

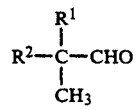

where $R^1$ and $R^2$ are each $C_1$–$C_4$-alkyl, are prepared by hydroformylation of 1,1-dialkylethylenes II

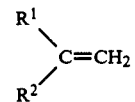

with cobalt carbonyl complexes, entailing
(a) carrying out the reaction in the presence of water-containing solvents in which water is soluble or at least partially soluble, with the water content of the reaction mixture being from 0.1 to 20% by weight, or
(b) carrying out the reaction in the presence of a lactone which can have one or more $C_1$–$C_4$-alkyl substituents, or of an aliphatic or cycloaliphatic sulfone.

4 Claims, No Drawings

PREPARATION OF 2,2-DIALKYLPROPIONALDEHYDES

The present invention relates to an improved process for the preparation of 2,2-dialkylpropionaldehydes of the general formula I

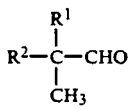

where $R^1$ and $R^2$ are each $C_1$–$C_4$-alkyl, by hydroformylation of 1,1-dialkylethylenes of the general formula II

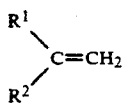

with cobalt carbonyl complexes. 2,2-Dialkylpropionaldehydes are important intermediates for a large number of organic syntheses, for example for the preparation of pharmaceuticals.

Chemical Engineering Progress, Vol. 62, No. 4, (1966) pp. 74–78 relates to the hydroformylation of isobutene in which the main product 3-methylbutyraldehyde is accompanied by a little pivaladehyde (2,2-dimethylpropionaldehyde). The best yield of pivalaldehyde was 5.2% achieved under a pressure of about 415 bar, at from 200° to 220° C. and with a concentration of the cobalt carbonyl catalyst of 0.26 to 0.28% by weight cobalt, based on isobutene, and with methanol or water as solvent. The percentage of pivalaldehyde is lower in water than in methanol.

Zhurnal Prikladnoi Khimii, Vol. 41, No. 10, (1968) pp. 2275–2281 states that the main product of the hydroformylation of isobutene with cobalt carbonyl complexes is likewise 3-methylbutyraldehyde. Pivalaldehyde is also produced in a yield of 5 to 6%.

According to Karbonilirovanie Nenasyshchennykh Uglevodorodov, (1968) pages 75–80 (Chemical Abstracts Reference Vol. 70 (1969) 114537f) the hydroformylation of isobutene in toluene with cobalt carbonyl complexes under about 290 bar, at 175° to 190° C. and with a concentration of the cobalt carbonyl complex of 0.65% by weight cobalt results predominantly in 3-methylbutyraldehyde, and in a pivalaldehyde yield of only about 5%.

Hence the object of the present invention was to increase the percentage of 2,2-dialkylpropionaldehydes I in the hydroformylation of 1,1-dialkylethylenes II.

Accordingly, we have found a process for the preparation of 2,2-dialkylpropionaldehydes I by hydroformylation of 1,1-dialkylethylenes II with cobalt carbonyl complexes, which comprises
(a) carrying out the reaction in the presence of water-containing solvents in which water is soluble or at least partially soluble, with the water content of the reaction mixture being from 0.1 to 20% by weight, or
(b) carrying out the reaction in the presence of a lactone which can have one or more $C_1$–$C_4$-alkyl substituents, or of an aliphatic or cycloaliphatic sulfone.

In embodiment (a) of the process according to the invention, the reaction is carried out in the presence of water-containing solvents, especially organic solvents in which water is soluble or at least partially soluble, it being necessary for the solubility under the reaction conditions to be not less than 1% by weight. The water content of the complete reaction mixture is from 0.1 to 20% by weight, preferably from 0.1 to 10% by weight, where the reaction mixture is defined as the mixture of the solvent with the catalyst and the olefin II.

The organic solvent normally comprises 40 to 80% by weight of the reaction mixture, and the recommended ratio of this solvent to water is in the range from 5:1 to 100:1, especially 10:1 to 100:1, by weight. It is additionally expedient for the ratio of the water-containing solvent to the olefin to be from 0.5:1 to 100:1, preferably 0.5:1 to 10:1, especially 1:1 to 10:1, by volume.

Suitable organic solvents in this connection are ketones, for example acetone, diethyl ketone, methyl ethyl ketone, diisopropyl ketone, methyl isopropyl ketone, acetophenone, benzophenone, cyclopentanone and cyclohexanone, cyclic ethers such as tetrahydrofuran and dioxane, carboxylic esters, for example ethyl acetate, ethyl propionate, methyl butyrate and methyl valerate, and hydroxyl-containing carboxylic esters such as ethyl 3-hydroxybutyrate and 3-hydroxy-2,2,4-trimethylpentyl isobutyrate.

Particularly good results are obtained with ketones.

In embodiment (b) of the process according to the invention, the olefin II is hydroformylated in the presence of a lactone, which may be substituted, or of an aliphatic or cycloaliphatic sulfone as solvent, in which case the ratio of this solvent to the olefin is 0.5:1 to 100:1, preferably 0.5:1 to 10:1, especially 1:1 to 10:1, by volume. It is also possible for other conventional organic solvents to be present, such as dioxane, tetrahydrofuran, cyclohexane, toluene or xylenes. Of course, it is also possible to use water-containing lactones or sulfones in this embodiment of the process—however, the presence of water in these solvents does not generally result in a further improvement in the results. The formation of the aldehydes I increases with an increasing percentage of lactone or sulfone compared with the olefins II in the reaction mixture, and it is therefore expedient to use an excess of these solvents.

Suitable lactones have 5, 6 or 7 ring members and may have one or more $C_1$–$C_4$-alkyl substituents. Typical representatives are γ-butyrolactone, δ-valerolactone and ε-caprolactone. It is most advantageous to employ lactones with 5 ring members, such as, in particular, γ-butyrolactone, 4-ethyl-γ-butyrolactone and 5-methyl-γ-butyrolactone (γ-valerolactone), but also 3-methyl-γ-butyrolactone, 4-methyl-γ-butyrolactone, 3,4-dimethyl-γ-butyrolactone, 4,5-dimethyl-γ-butyrolactone, 5-propyl-γ-butyrolactone or 3,5-diethyl-γ-butyrolactone.

Sulfones which can be used are dimethyl sulfone, diethyl sulfone, tetramethylene sulfone (sulfolane) or pentamethylene sulfone. Particularly good results are obtained with sulfolane.

The process according to the invention is particularly suitable in both embodiments for the preparation of pivalaldehyde (2,2-dimethylpropionaldehyde) from isobutene. However, it is also possible and advantageous to use this process to prepare other aldehydes of the general formula I, for example 2,2-dimethylbutyraldehyde, 2,2-dimethylvaleraldehyde, 2,2-dimethylisovaleraldehyde, 2,2-dimethylhexanal, 2-ethyl-2-methylbutyraldehyde, 2-ethyl-2-methylvaleraldehyde, 2-methyl-2-propylvaleraldehyde, 2-ethyl-2-methylhexanal, 2-methyl-2-propylhexanal and 2-butyl-2-methylhexanal, from the appropriate olefins II.

Apart from the features essential to the invention as specified in embodiments (a) and (b), the hydroformylation can be carried out in a conventional manner, discontinuously or continuously, i.e. under pressures of, normally, 60 to 330 bar, especially 130 to 280 bar, at, normally, from 60° to 200° C., especially 80° to 160° C., and with an amount of cobalt carbonyl catalyst of expediently 0.1 to 1% by weight, especially 0.2 to 0.5% by weight, cobalt, based on the total amount of the reaction mixture. As a rule, a water gas with a ratio of carbon monoxide to hydrogen of from 0.5:1 to 2:1 by volume is used, a ratio of 1:1 being particularly advantageous.

The catalysts used are cobalt carbonyl complexes which are normally soluble in the reaction mixture. The catalyst can be employed, for example, as a carbonyl compound such as $Co_2(CO)_8$, $Co_4(CO)_{12}$ and $HCo(CO)_4$ or as salt such as cobalt acetate, cobalt nitrate, cobalt carbonate and cobalt 2-ethylhexanoate. It is also possible to use cobalt oxides and metallic cobalt. The catalytically active carbonyl complexes are formed from the cobalt compounds and the cobalt with the water gas under the reaction conditions.

The reaction mixture which, as a rule, may contain other products in addition to the product I, such as aldehydes isomeric with I, products of reduction of the aldehydes which have formed, and products of addition of water onto the olefin II, as well as unreacted olefin II, is normally worked up in a conventional manner.

The 2,2-dialkylpropionaldehydes I are obtained in distinctly higher yields than previously possible by hydroformylation of the appropriate olefins II.

EXAMPLES 1 TO 9 AND COMPARATIVE EXAMPLES A AND B

Discontinuous Hydroformylation of Isobutene in Water-Containing Solvents 122 g of liquid isobutene were added to a solution of 6.5 g of dicobalt octacarbonyl in 400 g of one of the solvent/water mixtures listed in Table 1. A pressure of 100 bar was set up by injecting a $CO/H_2$ mixture in the ratio 1:1 by volume. After the temperature had been raised to 110° C., a pressure of 280 bar was set up by further injection of this gas mixture and was maintained throughout the reaction time of 3 hours. The cooled reaction mixture was analyzed, after the pressure had been released, by gas chromatography.

The results of these experiments are to be found in Table 1.

TABLE 1

(EXAMPLES 1 TO 9 AND COMPARATIVE EXAMPLES A AND B)

| Ex. No. | Solvent | Water in the reaction mixture [% by wt.] | Conversion [%] | PVA [%] | Yield of 3-MBA [%] | t-BuOH [%] |
|---|---|---|---|---|---|---|
| 1 | dioxane | 5.7 | 91 | 8.3 | 64.8 | 12 |
| A | dioxane | 0 | 75 | 2.3 | 50.2 | — |
| 2 | 3-hydroxy-2,2,4-trimethyl-pentyl isobutyrate | 3.0 | 94 | 5.1 | 60.0 | 4 |
| B | 3-hydroxy-2,2,4-trimethyl-pentyl isobutyrate | 0 | 89 | 2.0 | 57.0 | — |
| 3 | acetone | 0.2 | 94 | 15.2 | 31.7 | 7 |
| 4 | acetone | 5.7 | 97 | 26.7 | 41.0 | 26 |
| 5 | diisopropyl ketone | 0.15 | 87 | 3.6 | 59.0 | — |
| 6 | diisopropyl ketone | 2.8 | 91 | 7.9 | 56.5 | 8.5 |
| 7 | diethyl ketone | 0.12 | 82 | 6.8 | 46.2 | 0.5 |
| 8 | diethyl ketone | 2.8 | 89 | 12.6 | 44.5 | 1 |
| 9 | diethyl ketone | 5.7 | 93 | 17.5 | 42.5 | 17 |

PVA: pivalaldehyde, 3-MBA: 3-methylbutyraldehyde, t-BuOH: tert.-butanol

EXAMPLES 10 TO 14

Continuous Hydroformylation of Isobutene in Water-Containing Solvents

The hydroformylation of isobutene was carried out similarly to Examples 1 to 9 and Comparative Examples A and B under 280 bar and at 110° C. with a $CO/H_2$ mixture in the ratio 1:1 by volume continuously within 3 hours in the presence of the solvent/water mixtures listed in Table 2. This entailed 180 g/h of the said ketone/water mixture, which contained the dissolved $Co_2(CO)_8$ catalyst, and 61 g/h isobutene being pumped through the reactor. The cobalt content was 0.44% by weight based on the total reaction stream.

Table 2 shows the results of these experiments determined by gas chromatography.

TABLE 2

(EXAMPLES 10 TO 14)

| Ex. No. | Solvent | Water in the reaction mixture [% by wt.] | Conversion [%] | PVA [%] | Yield of 3-MBA [%] | t-BuOH [%] |
|---|---|---|---|---|---|---|
| 10 | acetone | 0.15 | 85 | 12.5 | 34.6 | 3.1 |
| 11 | acetone | 1.2 | 87 | 21.1 | 38.4 | 12.8 |
| 12 | acetone | 5.5 | 92 | 22.5 | 29.6 | 12.4 |
| 13 | diethyl ketone | 1.2 | 91 | 13.5 | 39.4 | 10.2 |
| 14 | diethyl ketone | 5.4 | 88 | 19.5 | 29.3 | 16.1 |

PVA: pivalaldehyde, 3-MBA: 3-methylbutyraldehyde, t-BuOH: tert.-butanol

EXAMPLES 15 TO 19 AND COMPARATIVE EXAMPLE C

Hydroformylation of Isobutene in the Presence of a Sulfone or Lactone 122 g of liquid isobutene (corresponding to 200 ml) were added to a solution of 7.6 g of dicobalt octacarbonyl in 400 g of one of the solvents listed in Table 3. A pressure of 100 bar was set up by injecting a $CO/H_2$ mixture in the ratio 1:1 by volume. After the temperature had been raised to 110° C., a pressure of 280 bar was set up by further injection of this gas mixture and was maintained throughout the reaction time of 3 hours. The cooled reaction mixture was analyzed, after the pressure had been released, by gas chromatography.

The results of these experiments are to be found in Table 3. The isobutene conversion was above 90% in each of Examples 15 to 19.

TABLE 3

(EXAMPLES 15 TO 19 AND COMPARATIVE EXAMPLE C)

| Example No. | Solvent | Solvent to isobutene ratio by vol. | Yield of PVA [%] | Yield of 3-MBA [%] |
|---|---|---|---|---|
| 15 | sulfolane | 1.57:1 | 27.8 | 2 |
| 16 | γ-butyrolactone | 1.81:1 | 25.2 | 6 |
| 17 | 5-methyl-γ-butyrolactone | 1.90:1 | 37.5 | 6 |
| 18 | 4-ethyl-γ-butyrolactone | 1.90:1 | 25.0 | 9 |
| 19 | ε-caprolactone | 1.94:1 | 17.2 | 3 |
| C | tetrahydrofuran | 2.25:1 | 6.4 | 74.2 |

PVA: pivalaldehyde, 3-MBA: 3-methylbutyraldehyde

EXAMPLES 20 TO 22 AND COMPARATIVE EXAMPLES D AND E

Hydroformylation of Isobutene in the Presence of Sulfolane and Toluene

The hydroformylation of isobutene was carried out similarly to Examples 15 to 19 and Comparative Example C under 280 bar and at 110° C. with a $CO/H_2$ mixture in the ratio 1:1 by volume within 3 hours in the presence of sulfolane and of varying amounts of toluene. The volume of 600 ml of reaction mixture, consisting of 122 g of liquid isobutene (corresponding to 200 ml) and 400 ml of solvent, ignoring the volume of the catalyst, in the reactor was kept constant during this, and sulfolane was increasingly replaced by toluene. The amount of the catalyst $Co_2(CO)_8$ was 4.6 g in each of Examples 20 to 22 and Comparative Examples D and E.

Table 4 shows details and the results of these experiments found by gas chromatography. At sulfolane/isobutene ratios below 0.5:1 the yields of pivalaldehyde merely corresponded to the state of the art.

TABLE 4

(EXAMPLES 20 TO 22 AND COMPARATIVE EXAMPLES D AND E)

| Example No. | Volume of sulfolane [ml] | Volume of toluene [ml] | Sulfolane to isobutene ratio by volume | Yield of PVA [%] | Yield of 3-MBA [%] |
|---|---|---|---|---|---|
| 20 | 400 | 0 | 2:1 | 19 | 2 |
| 21 | 200 | 200 | 1:1 | 17 | 35 |
| 22 | 100 | 300 | 0.5:1 | 8 | 56 |
| D | 50 | 350 | 0.25:1 | 4 | 62 |
| E | 0 | 400 | — | 2 | 54 |

PVA: pivalaldehyde, 3-MBA: 3-methylbutyraldehyde

We claim:

1. In a process for the preparation of 2,2-dialkylpropionaldehydes of formula I

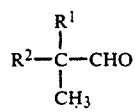

wherein $R^1$ and $R^2$ are each $C_1$-$C_4$-alkyl, by hydroformylation of 1,1-dialkylethylenes of formula II

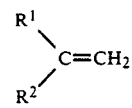

wherein $R^1$ and $R^2$ are defined as above, with cobalt carbonyl complex catalysts, formed from cobalt or cobalt compounds and water gas under the reaction conditions the improvement which comprises (a) carrying out said reaction in the presence of a water-containing solvent in which water is soluble or at least partially soluble, with the water content of the reaction mixture being from 0.1 to 20% by weight, or (b) carrying out said reaction in the presence of a lactone which can have one or more $C_1$-$C_4$-alkyl substituents, or of an aliphatic or cycloaliphatic sulfone.

2. A process for the preparation of 2,2-dialkylpropionaldehydes as claimed in claim 1, wherein the reaction in embodiment (a) is carried out with the reaction mixture containing from 0.1 to 10% by weight of water.

3. A process for the preparation of 2,2-dialkylpropionaldehydes as claimed in claim 1, wherein the reaction in embodiment (b) is carried out with a ratio of the lactone or sulfone to II of 0.5:1 to 100:1 by volume.

4. The process of claim 1 wherein said cobalt or cobalt compound is selected from the group consisting of $Co_2(CO)_8$, $Co_4(CO)_{12}$, $HCo(CO)_4$, cobalt acetate, cobalt nitrate, cobalt carbonate, cobalt 2-ethylhexanoate, cobalt oxides, and metallic cobalt, or a mixture thereof.

* * * * *